US008702806B2

(12) United States Patent
Balay et al.

(10) Patent No.: US 8,702,806 B2
(45) Date of Patent: Apr. 22, 2014

(54) ACETABULAR IMPLANT AND METHOD FOR THE PRODUCTION OF SAID IMPLANT

(75) Inventors: Bruno Balay, Trevoux (FR); Jean-Claude Cartillier, Lyons (FR); Claude Charlet, Saint Didier Au Mont d'Or (FR); Jean-Christophe Chatelet, Jassans (FR); Michel-Henri Fessy, Saint Genis Laval (FR); Louis Hovy, Mühltal-Traisa (DE); Alain Machenaud, La Balme de Sillingy (FR); Jean-Marc Semay, Saint Priest en Jarez (FR); Louis Setiey, Gleize (FR); Jean-Pierre Vidalain, Annecy le Vieux (FR); Ulrich Witzel, Wuppertal (DE); Sylvain Zanello, Mions (FR)

(73) Assignee: Depuy (Ireland) Limited, County Cork (IE)

( * ) Notice: Subject to any disclaimer, the term of this patent is extended or adjusted under 35 U.S.C. 154(b) by 1244 days.

(21) Appl. No.: 10/566,180

(22) PCT Filed: Jul. 29, 2004

(86) PCT No.: PCT/FR2004/002045
§ 371 (c)(1),
(2), (4) Date: Jan. 18, 2007

(87) PCT Pub. No.: WO2005/011537
PCT Pub. Date: Feb. 10, 2005

(65) Prior Publication Data
US 2007/0162146 A1 Jul. 12, 2007

(30) Foreign Application Priority Data

Jul. 30, 2003 (FR) ...................................... 03 09405

(51) Int. Cl.
*A61F 2/34* (2006.01)

(52) U.S. Cl.
USPC ...................................... 623/22.31; 623/22.32

(58) Field of Classification Search
USPC ....................................................... 623/22.31
See application file for complete search history.

(56) References Cited

U.S. PATENT DOCUMENTS

| 3,840,904 | A | * | 10/1974 | Tronzo | ........................ | 623/22.32 |
| 4,883,491 | A | | 11/1989 | Mallory et al. | | |
| 5,147,407 | A | * | 9/1992 | Tager | ......................... | 623/22.27 |
| 5,358,532 | A | * | 10/1994 | Evans et al. | ................. | 623/22.23 |

(Continued)

FOREIGN PATENT DOCUMENTS

| DE | 35 35 959 | 4/1987 |
| DE | 42 11 343 | 10/1993 |

(Continued)

*Primary Examiner* — Bruce E Snow
*Assistant Examiner* — Melissa Hoban
(74) *Attorney, Agent, or Firm* — Young & Thompson

(57) ABSTRACT

A cotyloid implant including a screwable cup receiving an articular insert. The cup is provided with screwing elements (11) on the periphery thereof and more particularly in the equatorial area (2) thereof, the elements being used to penetrate the bone material of the acetabular cup during screwing. The cup includes an osteointegration-facilitating coating such as a selective calcium hydroxyapatite coating. The coating (16) is a thick coating on the convex parts of the outer surface of the cup, including areas or valleys or hollow thread elements which are left free in the screwing elements. The coating is not as thick (17) on raised areas or screw thread areas.

21 Claims, 4 Drawing Sheets

(56) References Cited

U.S. PATENT DOCUMENTS

| | | | | |
|---|---|---|---|---|
| 5,360,448 A | * | 11/1994 | Thramann | 606/60 |
| 5,443,520 A | * | 8/1995 | Zweymuller et al. | 623/22.31 |
| 5,478,237 A | * | 12/1995 | Ishizawa | 433/201.1 |
| 5,505,736 A | | 4/1996 | Reimels et al. | |
| 5,702,473 A | * | 12/1997 | Albrektsson et al. | 623/22.31 |
| 5,782,929 A | * | 7/1998 | Sederholm | 623/22.34 |
| 5,885,079 A | * | 3/1999 | Niznick | 433/174 |
| 5,972,032 A | * | 10/1999 | Lopez et al. | 623/22.32 |
| 6,146,425 A | * | 11/2000 | Hoermansdoerfer | 623/22.31 |
| 6,231,612 B1 | * | 5/2001 | Balay et al. | 623/22.31 |
| 2003/0050705 A1 | * | 3/2003 | Cueille et al. | 623/22.24 |
| 2005/0267585 A1 | * | 12/2005 | Sidebotham | 623/22.28 |

FOREIGN PATENT DOCUMENTS

| | | |
|---|---|---|
| DE | 43 36 551 | 3/1995 |
| EP | 0 578 345 | 1/1994 |
| EP | 0 887 052 | 12/1998 |
| EP | 1 151 732 | 11/2001 |
| FR | 2 688 402 | 9/1993 |
| FR | 2 748 201 | 11/1997 |
| WO | WO 95/17140 | 6/1995 |
| WO | WO 01/45585 | 6/2001 |

* cited by examiner

ACETABULAR IMPLANT AND METHOD FOR THE PRODUCTION OF SAID IMPLANT

BACKGROUND OF THE INVENTION

1. Field of the Invention

The present invention relates to an acetabular implant, that is to say, the component intended to be implanted in the acetabulum, within the context of a hip prosthesis. The invention also relates to a method for producing that implant.

2. Description of the Related Art

Acetabular implants generally comprise a small cup which is intended to be introduced and secured in the acetabulum of the hip joint and an insert, in a fixed or movable state in the cup, which forms the seat of the joint of the prosthetic femoral head. The cups which are generally composed of a biocompatible metal, such as titanium, can be secured in the cotyloid cavity using cements. When securing without any cement is selected, it is necessary to bring about primary securing of the cup in the cotyloid cavity, that securing optionally being supplemented, in particular in the case of replacement of the prosthesis, by auxiliary means, such as screws, hooks or closing tabs.

However, there must then be obtained secondary securing by osteointegration, by means of healing osteogenesis, which will prolong the stability of the implant in the bone site of the acetabulum, with remodelling under permanent stress.

SUMMARY OF THE INVENTION

The primary mechanical securing can be brought about either by impaction, using, as necessary, cups having a surface effect in order to obtain adjustment by means of pressure, or by a screwing action, the cups then being provided with means, such as threads, allowing a screwing action in the acetabular bone. Efforts are made to facilitate that osteointegration either by roughening the surface of the cup, for example, with the action of sand or corundum, or by covering the cup with a compatible coating with an osteointegrating effect which is generally a calcium hydroxyapatite ceramic material.

An object of the present invention is to improve screw type cups which are coated with an osteointegrating material, such as a hydroxyapatite ceramic material.

In particular, the invention facilitates the primary securing by means of screwing and adjustment of those cups and improves, after initial stabilisation, the secondary securing by means of osteointegration, involving true healing osteogenesis which will prolong the stability of the implant in a bone site, with permanent remodelling.

It also reduces the degree of bone traumatism during securing by means of screwing.

Finally, it reduces or obviates the risks of splinters being formed from the coating.

The invention relates to an acetabular implant of the type comprising a small screw type cup which receives an articular insert, the cup having, at the periphery, and in particular in the tropical/equatorial zone thereof, screwing means which are intended to be introduced into the bone material of the acetabulum during the screwing action, the cup carrying a coating which facilitates osteointegration, such as, in particular, a selective calcium hydroxyapatite coating, characterized in that the coating is of the thick type on the convex portions of the outer surface of the cup, including in the zones or troughs or recesses of threads that are left free in the screwing means, whilst that coating has a lesser thickness, or is even absent, on the screw reliefs or threads.

Coating of a thick type is intended to refer to a conventional coating thickness, as is generally known on coated cups or other prostheses which are coated with a layer of an osteointegrating coating. In the case of calcium hydroxyapatite, that thickness of a coating of a thick type is preferably in the order of from 100 to 200 micrometers, in particular advantageously in the order of 150±35 micrometers, those indications not being limiting and being dependent on the type and quality of the osteointegrating coating.

In accordance with the invention, it will be understood that this thickness may be as high as the entire value allowed in a stable intra-osseous implantation position, which is mainly subjected to compression loads.

The screw reliefs, such as threads, may then either have no coating at all or, preferably, have a thinner coating which may advantageously, in the case of hydroxyapatite, be in the order of 50±30 micrometers.

It will be appreciated that there will thus be provided important osteointegration characteristics in the region of the thick coating layer on the convex portions of the cup, including between the threads, the coating layer scarcely being subjected to any shearing forces during the screwing of the cup and contact being brought about without any traumatism at the end of the screwing action, when locking is brought about in the cotyloid cavity.

On the sides of threads or reliefs, the lesser thickness of the coating improves the shearing strength of that coating and therefore reduces the risks of delamination during the screwing action, whilst at the same time bringing about excellent mechanical engagement and also allowing improved osteointegration owing to the presence of the hydroxyapatite.

Should hydroxyapatite not be provided on the threads, the sides of threads are advantageously roughened with the action of sand or corundum, also improving contact osteogenesis.

In a particularly preferred configuration of the invention, the screwing means, such as threads, is arranged in order to traumatize as little as possible the acetabular zone in which the threads are introduced, and in order to have a maximum convex surface-area, that is to say, troughs between the sides of threads in order to facilitate, in this region, osteointegration by contact osteogenesis and remodelling under stress.

In accordance with that improved configuration, the screw relief is arranged in order to apply a self-tapping cutting effect during the screwing action and an effect involving compression of the sponge-like bone.

In a particularly preferred manner, the threads which are arranged on the tropical/equatorial zone of the cup, have a narrow cross-section in order to leave a maximum surface-area between two crests of consecutive threads, the proportion of the thickness of a thread relative to the corresponding pitch preferably being from 0.2 to 0.5.

Preferably, the cross-section of the threads is asymmetrical in a diametrical plane, with a smaller angle, for example, in the order of from 5 to 10° at the polar side of the thread, that is to say, a thread near the horizontal, in order to act counter to the introduction, and a greater angle, for example, in the order of from 15 to 20° at the equatorial side, in order to bring about a good compression effect when the bone which receives the threading is placed under stress.

Also in an advantageous manner, the crests of threads are relieved, with a leading edge which is radially higher than the remainder of the crest, whose radial height preferably decreases in a progressive manner towards the rear of the thread.

The leading edge is itself preferably inclined, by being formed by a milling pass which is strongly inclined in a biased manner relative to the inclination of the threading itself, the leading edge itself preferably being orientated aggressively forwards relative to the radial.

The pitch of the threading is advantageously regular in order to bring about a single bone groove, in which successive threads are introduced during the screwing rotation.

Preferably, the height of the threads, or more precisely the orientation of the crests, in the entirety of the zone, is constant, it being understood that, when a replacement cup is involved, that height will be greater in order to allow screwing into a more irregular cotyloid cavity, with bone of lesser quality.

The cup also preferably has completely spherical convexity, including between the successive reliefs, thereby allowing excellent adaptation against the bottom of a cotyloid cavity obtained after milling, when the cup arrives at the end of the screwing action.

In a very advantageous configuration of the invention, it is possible to use, for example, a form of threading such as that described in patent applications EP-A-0887052 and DE-A-19727846, in particular in FIGS. 9 to 14 of EP 98250211, the drawings and the description of that application being incorporated herein by reference.

The invention also relates to a method for producing the implant cups according to the invention, wherein a cup is produced, for example, from titanium alloy, having a threading in the tropical/equatorial zone thereof, the outer surface of the cup is processed in order to roughen it, for example, with the action of sand or corundum, and a coating of osteointegrating-material, such as, and in particular, calcium hydroxyapatite, is positioned on that cup surface, characterized in that the step for coating with osteointegrating material is carried out so as to bring about a thick deposit on the convex surfaces of the cup, including the troughs which separate the adjacent threads, and with the coating with that material on the sides and edges of the threads being reduced or omitted.

In the conventional case, in which a plasma type torch is used in order to project and secure, on the rough surface of the cup, the material which is intended to form that coating, it is advantageously possible to reduce the thickness of the deposit forming the coating on the threads by temporarily modifying the angle of inclination of the torch and/or by modifying the relative travel speed between the torch and the cup.

In a preferred embodiment, the invention relates to a method for producing implant cups according to the invention, characterized by the following steps:
  the number of cups which are or are not coated with calcium hydroxyapatite to be produced is established beforehand, optionally with modification during the production operation;
  the non-coated cups are produced and they are subjected to a processing operation which is intended to roughen the surface thereof;
  in the overall production established in this manner, the proportion of cups which are intended to receive a coating of osteointegrating material, such as calcium hydroxyapatite, is established;
  the coating of that cup is carried out in accordance with the invention;
  all the cups are packaged and sterilized in order to be contained in individual sterile packagings, the packagings having different markings in order to distinguish the coated cups from the non-coated cups.

The total number of cups to be produced is established in conventional manner, either by forecasting or by centralizing the orders, or both.

Establishing the proportion of cups to be coated in relation to the cups which are not coated is preferably carried out during the production operation and, if necessary, modified in accordance with the progress of events.

Those operations can be carried out using data-processing means which may optionally intervene in the control of the production means.

BRIEF DESCRIPTION OF THE DRAWING FIGURES

Other advantages and features of the invention will be appreciated from a reading of the following description which is given by way of non-limiting example with reference to the appended drawings, in which.

DETAILED DESCRIPTION OF THE INVENTION

The cup illustrated is generally in the form of a hemispherical member having a polar outer surface 1 without any relief and an outer inter-tropical/equatorial zone 2 having the threading. A polar hole 3, which is generally used for the auxiliary positioning members, is provided at the very pole of the cup.

Figure 2:
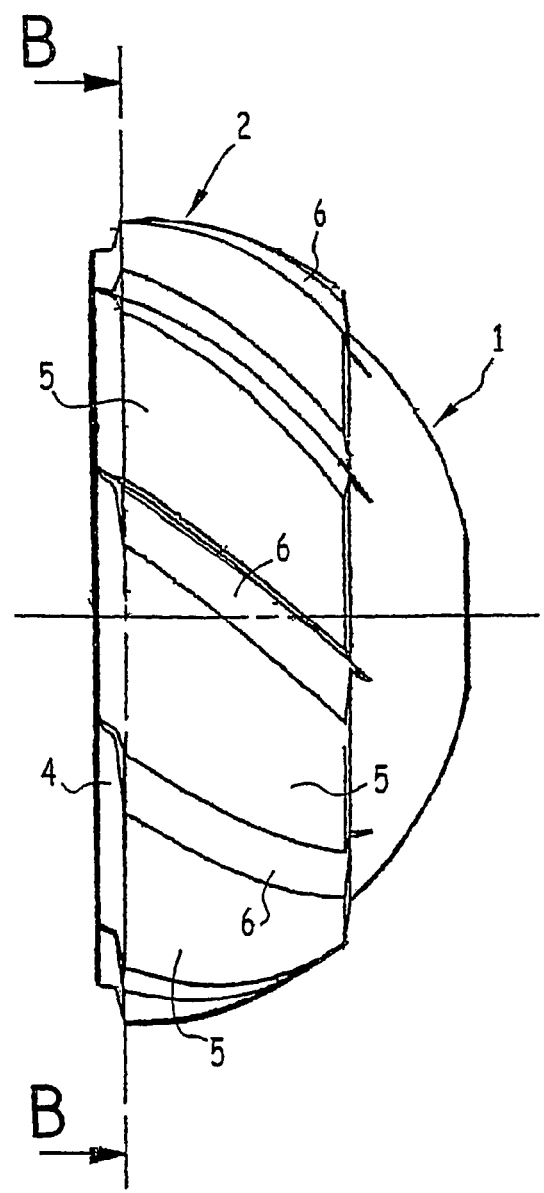
FIG. 2 is an elevation of that cup.
Figure 3:
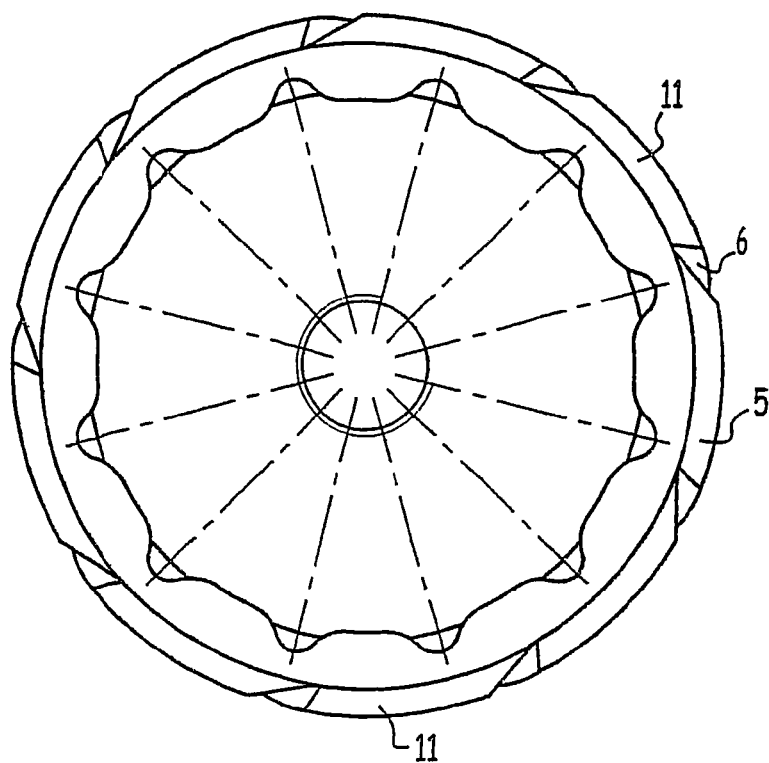
FIG. 3 is a bottom view of that cup.
Figure 4:
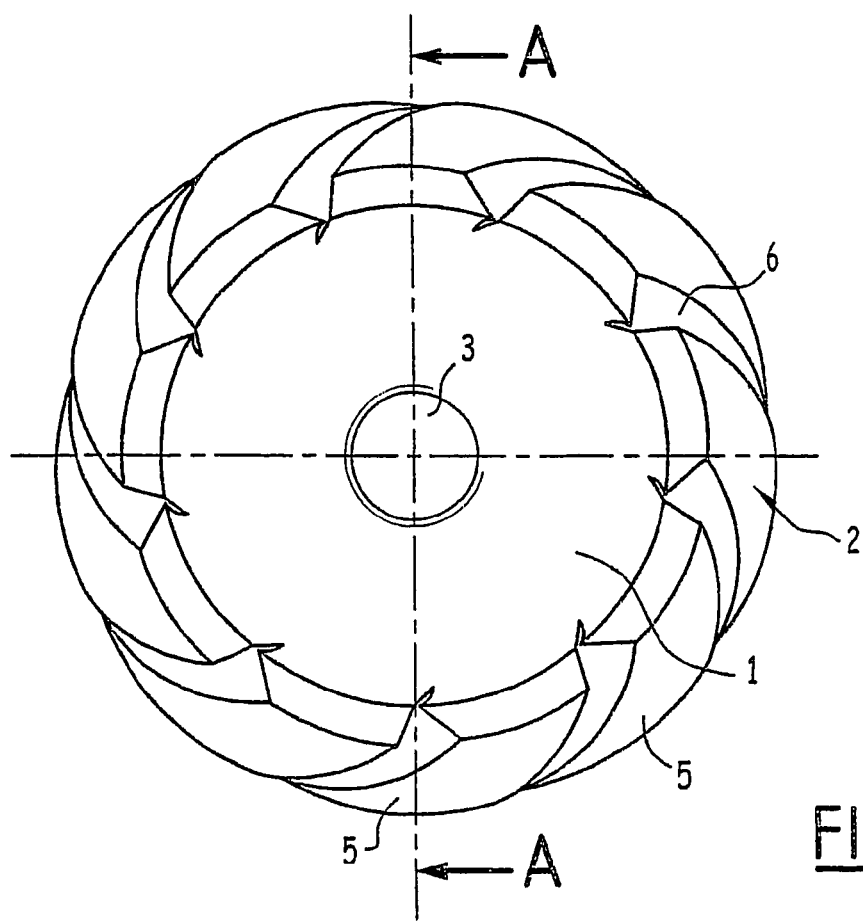
FIG. 4 is a top view of the cup.

With reference most particularly to FIG. 2, it is apparent that the equatorial zone carrying the screwing means extends with little spacing from the base 4 of the cup and that that equatorial zone is itself divided into a plurality of zone segments 5 by helical millings 6 over the sphere, which are intended to form the self-tapping leading edges of the threads of the threading of the zone 2.

Figure 1:
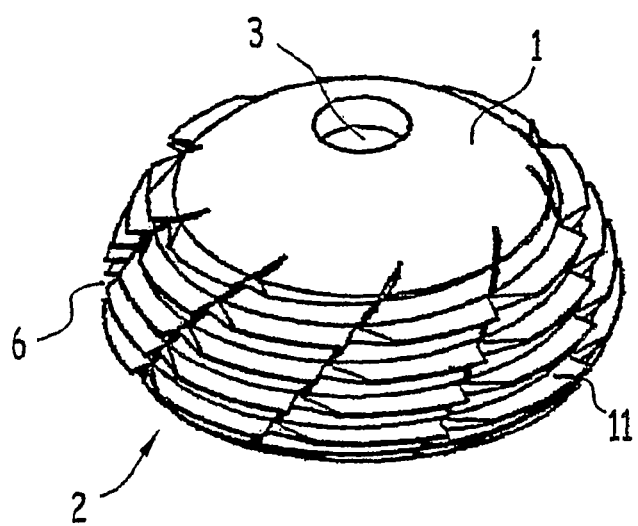
FIG. 1 is a perspective view of an implant cup according to the invention.
Figure 5:
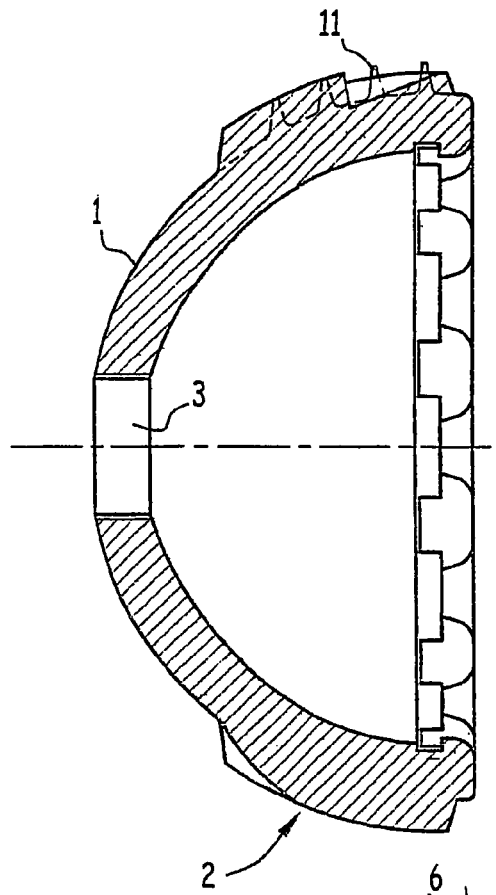
FIG. 5 is an axially sectioned view of the cup.
Figure 6:
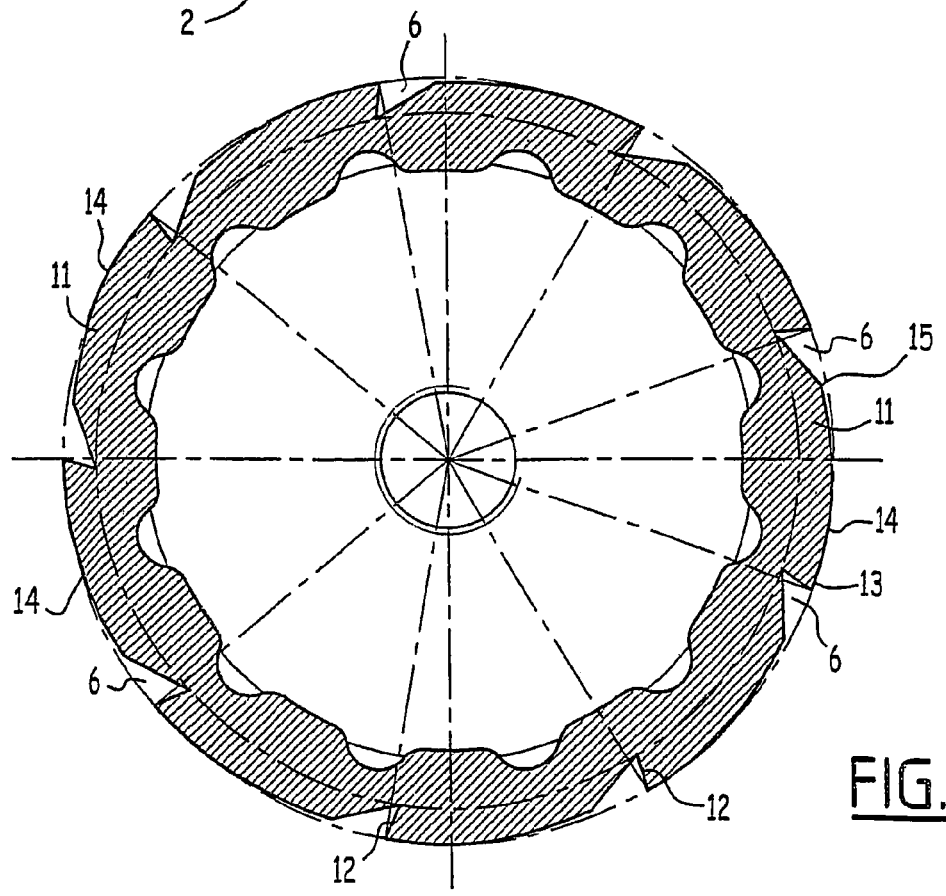
FIG. 6 is a section taken along line B-B of FIG. 2.
Figure 7:
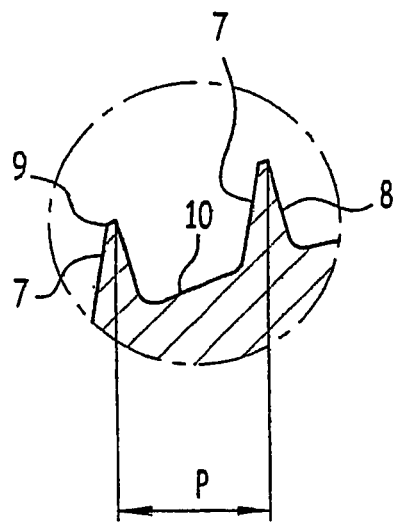
FIG. 7 is a radially sectioned view, from FIG. 5, of a detail, drawn to an enlarged scale in the region of the threading.

In the majority of the Figures, the individual threads are not illustrated, but they can clearly be seen in FIGS. 1, 5, 7 as can the most equatorial threads in FIG. 6.

In the example illustrated, the threading forms a single spherical helix, that is to say, a helix which is formed at the surface of the sphere of the cup and which has a constant pitch P which is defined at the axis of revolution and which extends through the pole of the cup. The threads themselves have a constant inclination relative to that axis. More precisely, as can be seen in FIG. 7, the polar sides 7 have an inclination which is less than that of the equatorial sides 8, the inclination of the polar sides being from 5 to 10° and that of the equatorial sides being from 15 to 20°, relative to the radial plane which is perpendicular to the polar axis. The thread tops or crests are slightly chamfered. Finally, it is apparent that the grooves or thread bottoms 10 have a width which is greater than that of the base of the threads, in order to provide a maximum spherical convex surface-area between the threads.

The form of the individual threads 11 is more clearly visible in FIG. 6. Each thread 11 extends between two successive millings 6 and has in particular the following features.

The leading tooth is defined by the milled groove 6, the milling being such that the edge of the tooth extends inwards and towards the rear in order to form a cutting edge that is inclined with an aggressive tip 13, the edge forming, with the tangent relative to the tip 13, an angle of less than 90°. It will further be appreciated that, since the milling pass 6 is inclined, as is visible in FIGS. 1 and 2, the cutting face of the tooth, which extends upwards in a polar direction from the edge 12, is directed in a polar direction in order to form a cutting face located in a plane which is not perpendicular to the plane of FIG. 6.

The radial height of the crest 14 of the thread 11 diminishes progressively from the tip 13 towards the end 15 of the edge, as is clearly visible in FIG. 6, so that the crest 14 forms a relief which is progressively recessed relative to the groove bottom which is tapped by the tip 13 in the acetabular bone.

By means of those features, it is possible both to obtain an excellent clean cut which defines the grooves and to reduce the friction forces during the self-tapping screwing action, whilst the continuation of the screwing action, owing to the inclinations of the sides of threads, brings about the desirable compression effort on the bone which is received between the threads.

Once the cup has been produced and the threads machined in accordance with the above-mentioned feature, the cup is subjected to surface processing by the action of corundum, the whole of the surface of the cup, including the threads, thus receiving the desired degree of roughness which can be defined as follows: RT 25 micrometers minimum.

Subsequently, there is carried out, by means of a plasma torch, the projection of powdered calcium hydroxyapatite onto the outer surface of the cup. The formation of a calcium hydroxyapatite coating by this means is well known in the art and does not need to be described in greater detail. For example, a torch of the plasma torch type will be used at a distance of 100 mm from the surface, with a projection flow rate for calcium hydroxyapatite of 10 g/min and a relative displacement speed of the torch relative to the surface of 30 mm/s. For example, the torch follows a variable and optimized inclination.

Figure 8:
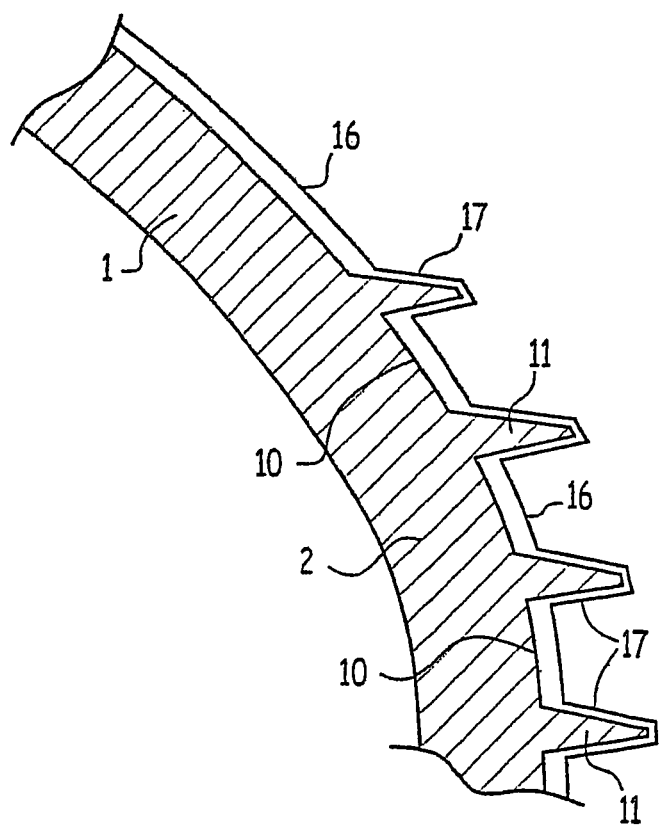
FIG. 8 is a schematic view illustrating the zones having a thick coating and the zones having a thin coating of calcium hydroxyapatite.

In accordance with the invention, a thick coating of hydroxyapatite having a substantially constant thickness which is advantageously 150 micrometers is produced over the entire spherical surface of the cup, that is to say, not only the polar zone 1, but also the threaded equatorial zone 2, that is to say, the troughs or thread bottoms 10. FIG. 8 schematically illustrates, by means of the line 16, this coating, that indication being, in its spherical portion, displaced in a homothetic manner relative to the surface of the spherical portion of the cup. The hydroxyapatite projection operation is, however, carried out in the region of the threads 11 so as to produce only a thin coating of 50 micrometers, represented by the line 17, which is also displaced relative to the actual surface of the cup. It is apparent in particular that that thin coating covers both the equatorial and polar faces and the crests of the threads 11.

For example, that thinner coating may be brought about by modifying the above-described parameters.

It is optionally possible, owing to the inclination of the torches, to bring about only a very thin coating, or even a practically non-existent coating, of the thread cutting face which extends from the front cutting edge 12.

In this manner, by means of the invention, it is possible to bring about very thick calcium hydroxyapatite coatings over the spherical convex zones which interact mechanically with the sponge-like subchondral bone, which is exposed completely by the hemispherical milling of the cotyloid cavity only towards the end of the screwing action, whereas, owing to the small thickness of hydroxyapatite on the threads themselves, the screwing torque is particularly reduced and, as a result, the damage to the subchondral bone is also reduced in direct contact with the threads, that conservation action being further increased by the provided shape of the threads which are thin and which have an upper relieved edge and an extremely sharp cutting edge.

The risk of the hydroxyapatite coating becoming detached or delaminating is also reduced, in particular in the region of the teeth, where the layer is subjected to the greatest effort, the thin layer being far more coherent, adhesively bonding better to the subjacent metal surface which has been acted upon with corundum.

The cup according to the invention, once in position, can receive any type of articular insert, for example, composed of polyethylene, aluminium or metal.

During the operation for producing a plurality of cups in accordance with the invention, it is advantageously possible to make provision for simultaneous production of the cups which are intended to receive the coating according to the invention and non-coated cups, as required, and to adjust, permanently, if desirable, the proportion between coated cups and non-coated cups, by directing towards the hydroxyapatite coating station a larger or smaller number of cups, the sterile packaging operations then being controlled in accordance with that proportion.

The invention claimed is:

1. An acetabular implant, comprising:
a screw cup configured to receive an articular insert;
screwing means having threads at a periphery or in a tropical/equatorial zone of the cup, the screwing means comprising screw reliefs, each screw relief having a polar face, an equatorial face and a crest, and said screwing means are intended to be introduced into bone material of the acetabulum during a screwing action; and
a coating carried by the cup, said coating facilitating osteointegration,
wherein the coating is a thick coating on convex portions of an outer surface of the cup, including on bottoms of said threads of said screwing means and the coating is a thin coating having a lesser thickness than said thick coating on the screw reliefs of said screwing means, the thin coating entirely covering both the equatorial and polar faces and the crests of the screwing means.

2. The implant according to claim 1, wherein a thickness of the thick coating is from 100 to 200 micrometers.

3. The implant according to claim 2, wherein the thickness of the thick coating is of an order of 150±35 micrometers.

4. The implant according to claim 1, wherein the thin coating of the screw reliefs are of an order of 50±30 micrometers.

5. The implant according to claim 1, wherein the screwing means is arranged to have thread bottoms between sides of threads to facilitate osteointegration, the screw reliefs being arranged to apply a self-tapping cutting effect during the screwing action and effect compression of the bone material.

6. The implant according to claim 5, wherein in a thread pitch, a proportion of thread width, in a region of the thread bottom, relative to the pitch, is from 0.2 to 0.5.

7. The implant according to claim 1, wherein a cross-section of the threads is asymmetrical in a diametral plane, with a smaller angle of an order of from 5° to 10° at a polar side of the thread, and a greater angle of an order of from 15° to 20° at an equatorial side, in order to bring about a good compression effect when the bone which receives the threading is placed under stress.

8. The implant according to claim 1, wherein crests of threads are relieved, with a leading edge which is radially higher than a remainder of the crest, whose radial height decreases towards a rear of the thread.

9. The implant according to claim 8, wherein the leading edge is itself inclined, by being formed by a milling pass which is strongly inclined in a biased manner relative to an inclination of the threading itself, the leading edge being orientated aggressively forwards relative to the radial.

10. The implant according to claim 1, wherein a threading pitch is regular in order to bring about a single bone groove, in which successive threads are introduced during the screwing action.

11. The implant according to claim 1, wherein the screwing means has a threading formed by zones of threads which are separated by inclined grooves defining cutting edges.

12. The implant according to claim 1, wherein the screwing means has a spherical threading of constant pitch.

13. The implant according to claim 1, wherein the coating is a selective calcium hydroxyapatite coating.

14. An acetabular implant, comprising:
a screw cup configured to receive an articular insert;
threads at a tropical/equatorial zone of the cup, said threads being intended to be introduced into bone material of the acetabulum during a screwing action, said threads comprising screw reliefs, each screw relief having a polar face, an equatorial face and a crest; and
a coating carried by the cup, said coating facilitating osteointegration,
wherein the coating is a thick coating on convex portions of an outer surface of the cup, including on thread bottoms of said threads, and the coating is a thin coating having a lesser thickness than said thick coating on the screw reliefs of the threads, the thin coating entirely covering both the equatorial and polar faces and the crests of the threads.

15. The implant according to claim 1, wherein the coating facilitating osteointegration is a selective hydroxyapatite coating.

16. The implant according to claim 14, wherein a thickness of the thick coating is from 100 to 200 micrometers.

17. The implant according to claim 16, wherein the thickness of the thick coating is of an order of 150±35 micrometers.

18. The implant according to claim 14, wherein the screw reliefs have a coating of an order of 50±30 micrometers.

19. The implant according to claim 14, wherein the threads are arranged to have thread bottoms between sides of the threads to facilitate osteointegration, the screw reliefs being arranged to apply a self-tapping cutting effect during the screwing action and effect compression of the bone material.

20. The implant according to claim 14, wherein the coating facilitating osteointegration is a selective hydroxyapatite coating.

21. An acetabular implant, comprising:
a screw cup configured to receive an articular insert;
threads at an equatorial zone of the cup, said threads being configured to be introduced into bone material of the acetabulum during a screwing action, said threads comprising screw reliefs, each screw relief having a polar face, an equatorial face and a crest; and
a coating carried by the cup, said coating facilitating osteointegration,
wherein the coating is from 100 to 200 micrometers on convex portions of an outer surface of the cup, including on thread bottoms of said threads, and the coating is of an order of 50±30 micrometers coating on the screw reliefs of the threads, the coating of an order of 50±30 micrometers entirely covering both the equatorial and polar faces and the crests of the threads.

* * * * *

UNITED STATES PATENT AND TRADEMARK OFFICE
CERTIFICATE OF CORRECTION

PATENT NO. : 8,702,806 B2
APPLICATION NO. : 10/566180
DATED : April 22, 2014
INVENTOR(S) : Balay et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1735 days.

Signed and Sealed this

Twenty-ninth Day of September, 2015

Michelle K. Lee
*Director of the United States Patent and Trademark Office*